(12) United States Patent
Hossain et al.

(10) Patent No.: US 8,062,845 B2
(45) Date of Patent: Nov. 22, 2011

(54) RAPID NUCLEIC ACID ISOLATION METHOD AND COMPOSITIONS

(75) Inventors: Ashfaque Hossain, Omaha, NE (US); Nancy Jo Dohse Hanson, Gretna, NE (US); Mark D. Reisbig, Omaha, NE (US)

(73) Assignee: Creighton University, Omaha, NE (US)

( * ) Notice: Subject to any disclaimer, the term of this patent is extended or adjusted under 35 U.S.C. 154(b) by 536 days.

(21) Appl. No.: 10/565,358

(22) PCT Filed: Jul. 21, 2004

(86) PCT No.: PCT/US2004/023269
§ 371 (c)(1),
(2), (4) Date: Nov. 20, 2006

(87) PCT Pub. No.: WO2005/010204
PCT Pub. Date: Feb. 3, 2005

(65) Prior Publication Data
US 2007/0077562 A1   Apr. 5, 2007

Related U.S. Application Data

(60) Provisional application No. 60/489,017, filed on Jul. 21, 2003.

(51) Int. Cl.
*C12Q 1/68* (2006.01)
(52) U.S. Cl. ...................................................... 435/6.1
(58) Field of Classification Search ......................... None
See application file for complete search history.

(56) References Cited

U.S. PATENT DOCUMENTS 5,346,994 A * 9/1994 Chomczynski ............... 530/419
5,777,099 A * 7/1998 Mehra ......................... 536/25.42

OTHER PUBLICATIONS

Cook et al. "Use of whole blood specimens for routine clinical quantitation of hepatitis C virus RNA does not increase assay sensitivity." J Clin Microbiol. Dec. 2000;38(12):4326-31.*
Cook et al. (J Clin Microbiol. Dec. 2000;38(12):4326-31).*
Majumdar et al. (Biotechniques. Jul. 1991;11(1):94-101).*

* cited by examiner

*Primary Examiner* — Christopher M. Babic
(74) *Attorney, Agent, or Firm* — Husch Blackwell LLP (57) ABSTRACT

A method of isolating RNA from a biological specimen is provided, whereby a biological specimen is contacted with an admixture of (i) a mono-phasic solution of phenol and guanidine isothiocyanate and (ii) a lysis buffer under conditions and for a time appropriate to form a homogenate. Next, the homogenate is admixed with a water-immiscible organic solvent under conditions and for a time appropriate to form an aqueous phase and an organic phase. The aqueous phase is then contacted with a $C_1$-$C_4$ lower alcohol under conditions and for a time to form a precipitated RNA. The precipitated RNA is then recovered by centrifugation and decanting of the aqueous phase. The method can also be used to isolate total RNA. In an alternative embodiment, the biological sample is contacted with (i) a lysis buffer, and (ii) a mono-phasic solution of phenol and guanidine isothiocyanate under conditions and for a time appropriate to form a homogenate. The remaining steps of this embodiment are the same as above.

14 Claims, 9 Drawing Sheets

RAPID NUCLEIC ACID ISOLATION METHOD AND COMPOSITIONS

CROSS-REFERENCE TO RELATED APPLICATIONS

This application is based on Ser. No. 60/489,017 filed on Jul. 21, 2003.

BACKGROUND OF THE INVENTION

Living cells contain various types of RNA, although three particular types make up the predominant proportion, namely ribosomal RNA (rRNA, approximately 80 percent of all RNAs in a cell), transfer RNA (tRNA, approximately 5 percent of all RNAs in a cell) and messenger RNA (mRNA, approximately 2-4 percent of all RNAs in a cell). A variety of other RNA types are known, including heterogeneous nuclear RNA (hnRNA), small cytoplasmic RNA (scRNA), small nuclear RNA (snRNA), small nucleolar RNA (snoRNA), regulatory RNAs, guide RNAs, telomerase RNA and small regulatory RNAs. Isolation of total RNA is typically designed to isolate substantially all of the three predominate types of RNA, that is rRNA, tRNA and mRNA, although minor amounts of the remaining RNA types can be present in the total RNA isolation.

High quality RNA is a prerequisite for various gene expression assays such as reverse transcriptase (RT) PCR, primer extension and Southern or Northern blotting techniques, as well as for preparation of RNA probes for these and similar techniques. In addition novel drug therapies require examining high quality RNA from many species of microbial pathogens. Methods of extracting RNA are known, but those methods have various undesirable characteristics.

Guanidinium thiocyanate and guanidinium chloride are known as effective protein denaturants, and the chloride salt has been employed as a deproteinization agent for isolating total RNA, see Cox, R. A.: Methods in Enzymology, 12(B): 120-129 (1968). In the Cox procedure, a suspension of ribosomes in a buffer is added to 6 molar guanidinium chloride. The RNA is precipitated by adding alcohol to the solution and the precipitate is recovered by centrifugation. At this point, the precipitate is not free of RNase (a contaminating enzyme that causes RNA degradation) and is purified by dissolution in 4 molar guanidinium chloride and re-precipitation by adding ethanol. The precipitate is again separated by centrifugation. If further purification is necessary, the precipitate is redissolved in guanidinium chloride and re-precipitated with ethanol. This procedure takes approximately two days to complete.

Another method for isolating total RNA is disclosed in Chirgwin, J. M. et al: Biochem, 18:5294-5299 (1979). In that procedure, RNA-containing tissue is homogenized in a solution containing guanidinium thiocyanate, sodium citrate and 2-mercaptoethanol, with the solution pH adjusted to 7 by adding sodium hydroxide. The homogenate is then centrifuged and the supernatant decanted and mixed with acetic acid (to lower the pH value to 5) and absolute ethanol. Overnight storage at −20° C. precipitates the RNA and it is recovered in pellet form after centrifugation. The pellet is redissolved in a buffered guanidine hydrochloride solution and reprecipitated by adding acetic acid and ethanol. The last step is repeated and the isolated RNA is recovered in pellet form.

Alternatively, the RNA can be separated from the guanidinium thiocyanate homogenate by ultracentrifugation through a dense cushion of cesium chloride. This method is disadvantageous in that it can take up to 2 days to obtain results and it can require the use of expensive ultracentrifugation equipment which reduces the total amount of RNA recoverable because of the limited number of samples that can be simultaneously processed.

Yet another RNA-isolating procedure is shown in Feramisco, J. R. et al: Molecular Cloning, 194-195, Cold Spring Harbor Laboratory, Cold Spring Harbor, N.Y. (1982), in which RNA-containing tissue is homogenized in a solution of 4M guanidinium isothiocyanate, 20% Sarkosyl™ (sodium lauryl sarkosinate) and 2-mercaptoethanol. An equal volume of heated phenol (approximately 60° C.) is added to the homogenate along with a sodium acetate solution of pH 5.2. Then an equal volume of chloroform is added and the mixture is cooled and centrifuged. The aqueous phase is recovered and reextracted with phenol and/or chloroform about seven more times before the final product is recovered. This procedure is slow and cumbersome in that multiple extractions are required and it takes approximately two days to recover the available RNA.

In U.S. Pat. No. 4,843,155, phenol and guanidine procedures were combined, resulting in a method of total RNA isolation that can be completed in 3 hours. The method of that patent was further improved upon in U.S. Pat. No. 5,346,994, which allows for completion of the RNA isolation in about 1 hour. Those methods involve the use of a mono-phasic solution of phenol and guanidine isothiocyanate, commercially available as the reagent Trizol® (Invitrogen Corp., Carlsbad, Calif.).

It has been found that total RNA samples extracted from clinical isolates using Trizol® or hot phenol methods can experience unacceptable levels of high molecular weight DNA contamination, as determined by ethidium bromide gel electrophoresis. That DNA contamination compromises the purity of the isolated RNA, making subsequent use of the RNA difficult or impossible. Unexpectedly, the methods and compositions of the present invention permit the easy preparation of highly pure RNA samples from clinical isolates with a minimum amount of contaminating genomic DNA. In addition, the methods and compositions of the present invention provide for higher yields and higher purity of total RNA isolated, when compared to other methods.

BRIEF SUMMARY OF THE INVENTION

In one aspect, the present invention contemplates a method of isolating RNA from a biological specimen by first contacting the biological specimen with an admixture of (i) a monophasic solution of phenol and guanidine isothiocyanate, and (ii) a lysis buffer, under conditions and for a time appropriate to form a homogenate. Next, the homogenate is admixed with a water-immiscible organic solvent under conditions and for a time appropriate to form an aqueous phase and an organic phase. The aqueous phase is then contacted with a $C_1$-$C_4$ lower alcohol under conditions and for a time to form a precipitated RNA. The precipitated RNA is then recovered, as by centrifugation and decanting of the aqueous phase.

In another aspect, the present invention contemplates a method of isolating RNA from a biological specimen by contacting the biological specimen with (i) a lysis buffer, and (ii) a mono-phasic solution of phenol and guanidine isothiocyanate, under conditions and for a time appropriate to form a homogenate. Next, the homogenate is admixed with a water-immiscible organic solvent under conditions and for a time appropriate to form an aqueous phase and an organic phase. The aqueous phase is then contacted with a $C_1$-$C_4$ lower alcohol under conditions and for a time to form a precipitated RNA. The precipitated RNA is then recovered, as by centrifugation and decanting of the aqueous phase.

In yet another aspect, the present invention contemplates a method of isolating total RNA from a biological specimen by first contacting the biological specimen with an admixture of (i) a mono-phasic solution of phenol and guanidine isothiocyanate and (ii) a lysis buffer under conditions and for a time appropriate to form a homogenate. Next, the homogenate is admixed with a water-immiscible organic solvent under conditions and for a time appropriate to form an aqueous phase and an organic phase. The aqueous phase is then contacted with a $C_1$-$C_4$ lower alcohol under conditions and for a time to form a precipitated total RNA. The precipitated total RNA is then recovered, as by centrifugation and decanting of the aqueous phase.

In a further aspect, the present invention contemplates a method of isolating total RNA from a biological specimen by contacting the biological specimen with (i) a lysis buffer, and (ii) a mono-phasic solution of phenol and guanidine isothiocyanate, under conditions and for a time appropriate to form a homogenate. Next, the homogenate is admixed with a water-immiscible organic solvent under conditions and for a time appropriate to form an aqueous phase and an organic phase. The aqueous phase is then contacted with a $C_1$-$C_4$ lower alcohol under conditions and for a time to form a precipitated total RNA. The precipitated total RNA is then recovered, as by centrifugation and decanting of the aqueous phase.

In a still further aspect, the present invention contemplates a method of isolating total RNA from a Gram-positive bacterium by contacting the Gram-positive bacterium with (i) a lysis buffer, and (ii) a mono-phasic solution of phenol and guanidine isothiocyanate, under conditions and for a time appropriate to form a homogenate. Next, the homogenate is admixed with a water-immiscible organic solvent under conditions and for a time appropriate to form an aqueous phase and an organic phase. The aqueous phase is then contacted with a $C_1$-$C_4$ lower alcohol under conditions and for a time to form a precipitated total RNA. The precipitated total RNA is then recovered, as by centrifugation and decanting of the aqueous phase.

Preferably, the biological specimen is a clinical isolate of a microorganism. The microorganism can be a bacterium, a virus, a fungus, or a combination thereof. The biological sample can be of human, animal, plant or microbial origin. Preferred bacteria are Gram-positive bacteria.

The lysis buffer comprises a chelating agent and a dispersing agent. In preferred embodiments, the chelating agent is EDTA. In other preferred embodiments, the chelating agent is EGTA. In an especially preferred embodiment, the chelating agent is a combination of EDTA and EGTA.

In preferred embodiments, the dispersing agent is a detergent. In another preferred embodiment, the dispersing agent is a surfactant. In an especially preferred embodiment, the surfactant is N-lauroylsarcosine. In another especially preferred embodiment, the surfactant is sodium lauryl sulfate.

Preferred water-immiscible organic solvents include chloroform and carbon tetrachloride. Preferred $C_1$-$C_4$ lower alcohols include ethanol, methanol and isopropyl alcohol.

In another aspect, the invention contemplates a composition of matter comprising an admixture of (i) a mono-phasic solution of phenol and guanidine isothiocyanate and (ii) a lysis buffer. This composition of matter is useful for isolating RNA or total RNA from a biological specimen.

In still another aspect, the invention contemplates a kit comprising an admixture of (i) a mono-phasic solution of phenol and guanidine isothiocyanate and (ii) a lysis buffer.

In a further aspect, the invention contemplates a kit comprising (1) a mono-phasic solution of phenol and guanidine isothiocyanate and (2) a lysis buffer.

Preferably, the kit contains instructions for isolating RNA or total RNA from a biological sample.

The lysis buffer comprises a chelating agent and a dispersing agent. In preferred embodiments, the chelating agent is EDTA. In other preferred embodiments, the chelating agent is EGTA. In an especially preferred embodiment, the chelating agent is a combination of EDTA and EGTA. In preferred embodiments, the dispersing agent is a detergent. In other preferred embodiments, the dispersing agent is a surfactant. In an especially preferred embodiment, the surfactant is N-lauroylsarcosine. In another especially preferred embodiment, the surfactant is sodium lauryl sulfate.

The present method has a number of benefits and advantages for the isolation of RNA and/or total RNA from biological specimens, including clinical microorganisms, without the use of hazardous materials as compared those methods that require the use of heated phenol, a dangerous corrosive material. The method of the invention is rapid and reproducible, yet provides yields comparable to other methods of nucleic acid isolation. The present method is economical and environmentally friendly, as it does not require the use of heated phenol or other components that are either costly or hazardous, and requires the use of less Trizol® than is currently necessary. The present method provides for preparation of RNA and/or total RNA samples that are substantially free from DNA contamination, as visualized by gel electrophoresis. The present method is suitable for extraction of RNA or total RNA from fresh clinical isolates of different species of microorganisms, such as viruses, bacteria, and fungi, including clinical isolates of *Escherichia coli, Salmonella enterica, Klebsiella pneumoniae, Enterobacter cloacae, Citrobacter freundii, Serratia marcescens, Pseudomonas aeruginosa, Staphylococcus aureus* and *Streptococcus pneumoniae*.

BRIEF DESCRIPTION OF THE DRAWINGS

FIG. 1 is shown on two sheets as FIG. 1A and FIG. 1B, in which FIG. 1A shows a photograph of a 1 percent agarose gel stained with ethidium bromide. The primary start sites of transcription were mapped using primer extension analysis as indicated by the arrow, using techniques set forth in the Examples elsewhere herein. The intensities of the bands were quantified using a Storm Molecular Imager with ImageQuant™ software (Molecular Dynamics Inc., Sunny, Calif., USA) and normalization of data was obtained using the 16S rRNA bands. Extension products were visualized by exposing the gel to a storage phosphor (Eastman Kodak Co., Rochester, N.Y., USA) for 2 days. The $bla_{ACT-1}$ and $bla_{MIR-1}$ sequencing ladders are represented on the left and right sides, respectively. The bands used to map the start site of transcription represent the amount of ampC RNA expression from each strain. These bands were quantified and normalized using the 16S rRNA bands. Lane 1 depicts the WTampC gene of *Enterobacter cloacae* strain 55. Lane 2 depicts the $bla_{ACT-1}$ gene of *Klebsiella pneumoniae* strain 255. Lane 3 depicts the $bla_{MIR-1}$ gene of *Klebsiella pneumoniae* strain 96D. Lane 4 depicts the ARampC gene of *Enterobacter cloacae* strain V 204.

FIG. 2 shows a photograph of three separate 1 percent agarose gel stained with ethidium bromide. Lanes 1-3 of the first gel (on the left) depict RNA samples isolated using the hot phenol method, as set forth in Example 2 elsewhere herein. Lanes 4-6 of the first gel depict RNA samples isolated using a Qiagen™ kit based on Trizol®, according to the manufacturer's instructions. The presence of high molecular weight DNA contamination can be seen in all six lanes. Lanes 2-5 of the middle gel show the results of RT-PCR of a *Pseudomonas aeruginosa* OprM gene. Lanes 2-5 of the third gel (on the right) show the results of RT-PCR of a *Pseudomonas aeruginosa* MexC gene. Lane 1 of the middle and third gels shows a 100 base pair molecular weight ladder.

FIG. 3 shows a photograph of a 1 percent agarose gel stained with ethidium bromide. Lanes 2-11 show the results of RT-PCR of *Enterobacter cloacae* ribosomal RNA using RNA samples isolated using a method of the invention. Lane 1 of the gel shows a 100 base pare molecular weight ladder.

FIG. 4 shows a photograph of a 1 percent agarose gel stained with ethidium bromide. Lanes 2-5 of the gel show the results of RT-PCR of a *Pseudomonas aeruginosa* efflux pump associated gene mexA using RNA samples isolated using a method of the invention. Lane 1 of the gel shows a 100 base pair molecular weight ladder.

FIG. 5 shows a photograph of a 1 percent agarose gel stained with ethidium bromide. Lanes 2-6 of the gel show a linearity curve of RT-PCR of the ampC gene from *Serratia marcescens* using RNA samples isolated using a method of the invention. Lane 1 of the gel shows a 100 base pair molecular weight ladder.

FIG. 6 shows a photograph of a 1 percent agarose gel stained with ethidium bromide. Lanes 1 and 2 depict RNA samples from clinical isolates of *Citrobacter freundii*. Lanes 3 and 4 depict RNA samples from clinical isolates of *Enterobacter cloacae*. Lanes 5 and 6 depict RNA samples from clinical isolates of *Escherichia coli*. All RNA samples were isolated using a method of the invention.

FIG. 7 shows a photograph of a 1 percent agarose gel stained with ethidium bromide. Lanes 2-5 depict a linearity curve of a *Pseudomonas aeruginosa* oprD gene. Lane 1 shows a 100 base pair molecular weight ladder. Determination of a linearity curve is part of the analysis for gene expression when the level of expression of several strains is compared. RT-PCR was carried out according to methods set forth in the Examples elsewhere herein, and samples were removed at the end of each cycle and resolved in the gel shown here in order to determine how many cycles the reaction should be allowed to proceed that permits optimal expression of the gene.

FIG. 8 shows a photograph of a 1 percent agarose gel stained with ethidium bromide. Lane A shows total RNA isolated from *Enterobacter cloacae* using a method of the invention. Lane B shows total RNA isolated from Enterobacter cloacae using Trizol®, according to the manufacturer's instructions except that a homogenizer was not used. Lane C is a 100 base pair molecular weight ladder.

DETAILED DESCRIPTION OF THE INVENTION

Figure 1A:
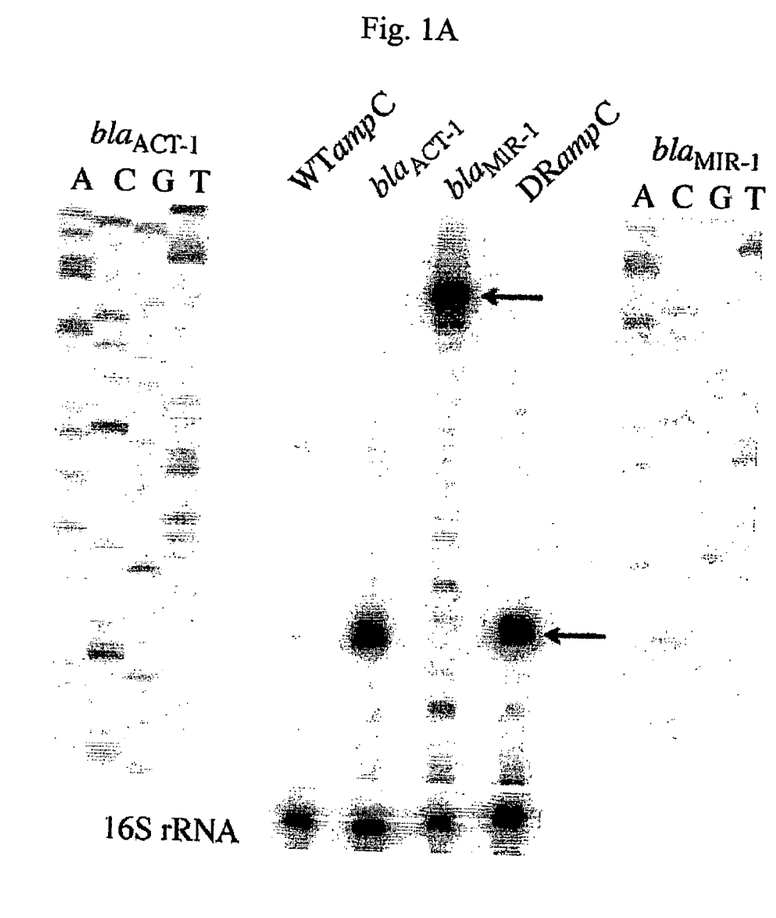
Figure 1B:
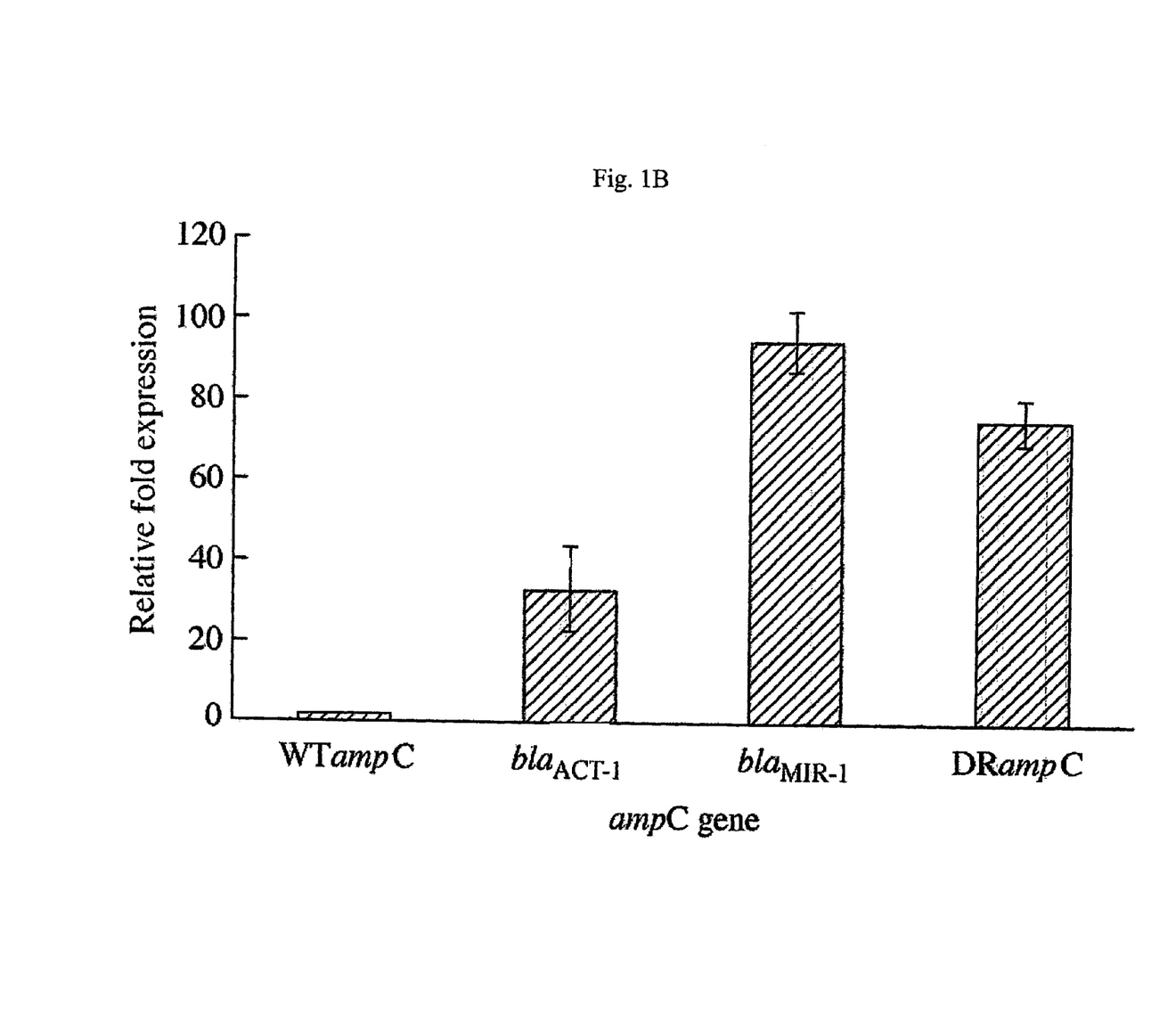
FIG. 1B shows a bar graph representing ampC expression of $bla_{ACT-1}$, $bla_{MIR-1}$ and DRampC relative to WTampC. Each value represents the mean of three experiments. Error bars represent the standard deviation.
Figure 2:
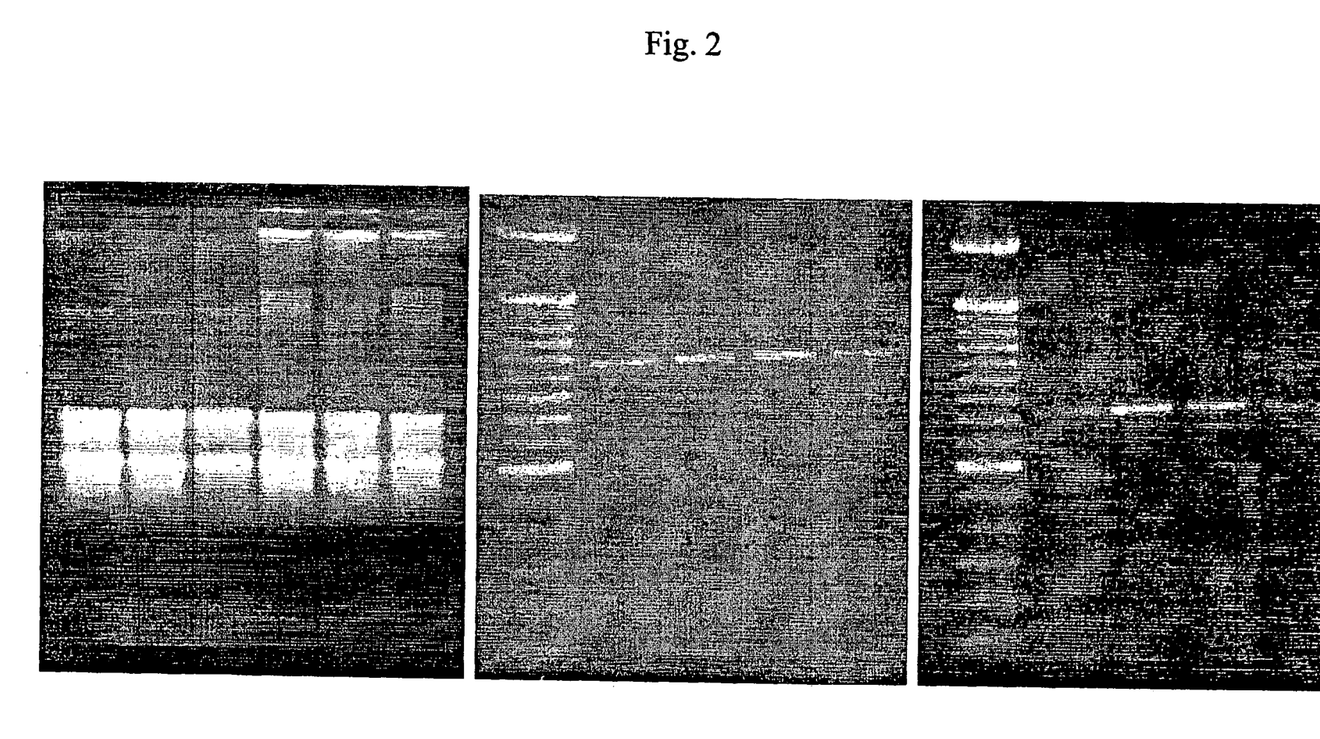
Figure 3:
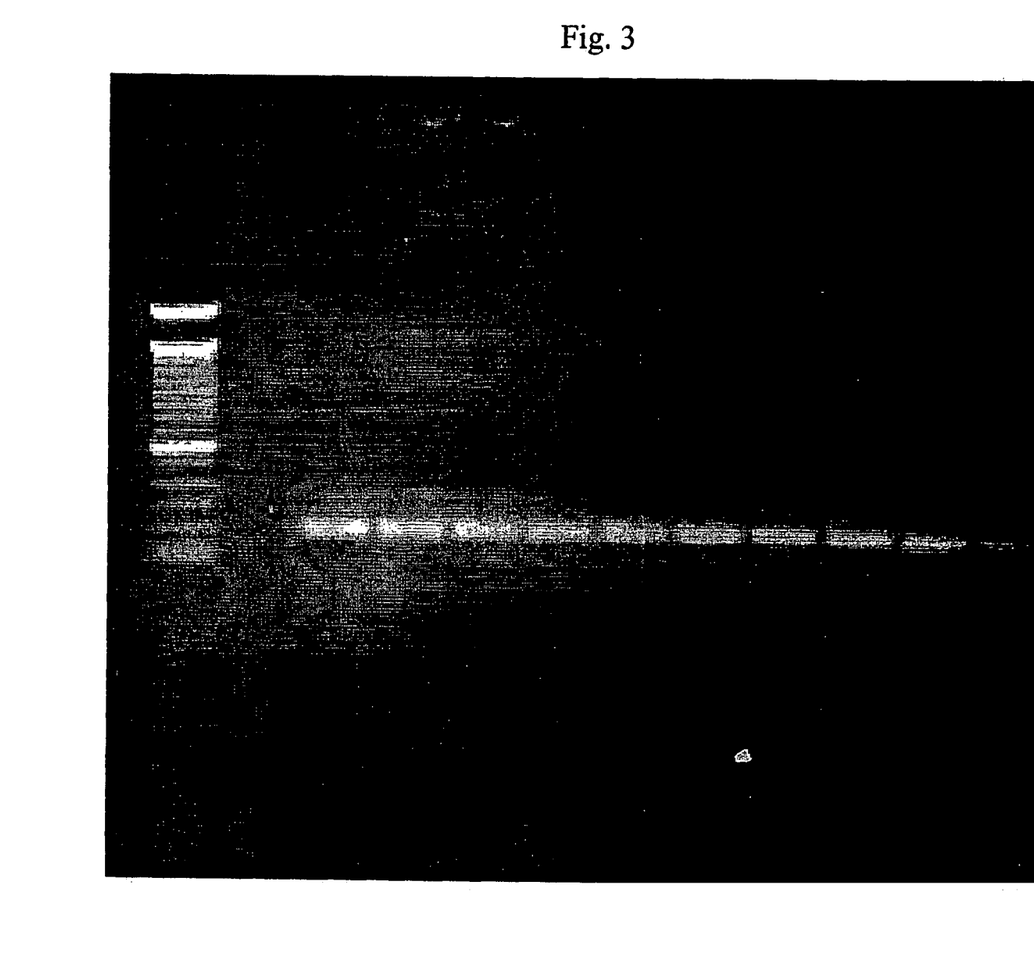
Figure 4:
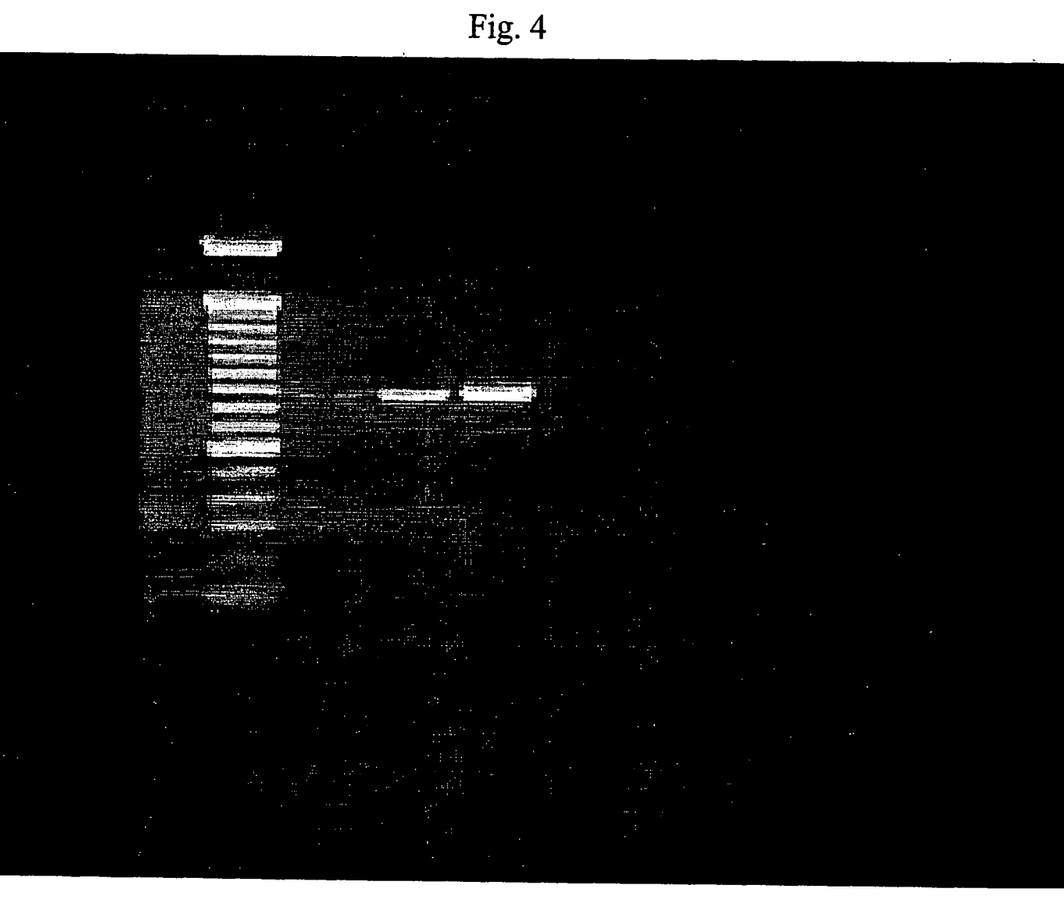
Figure 5:
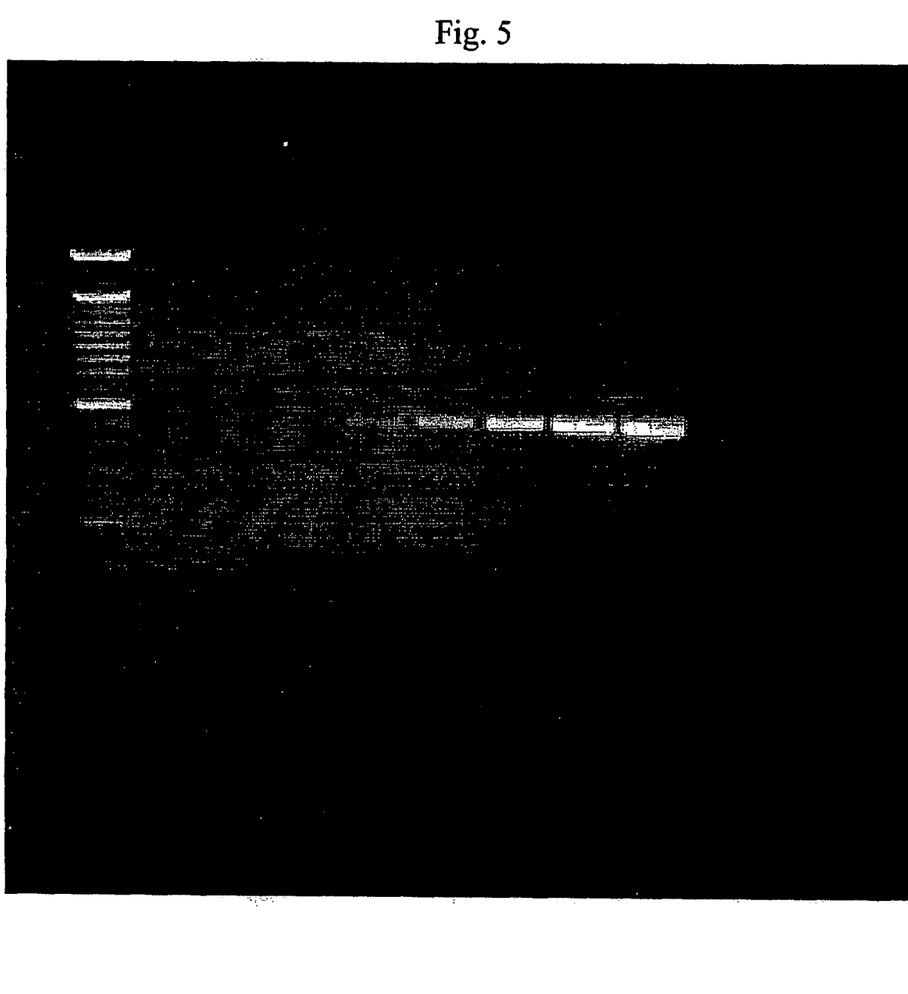
Figure 6:
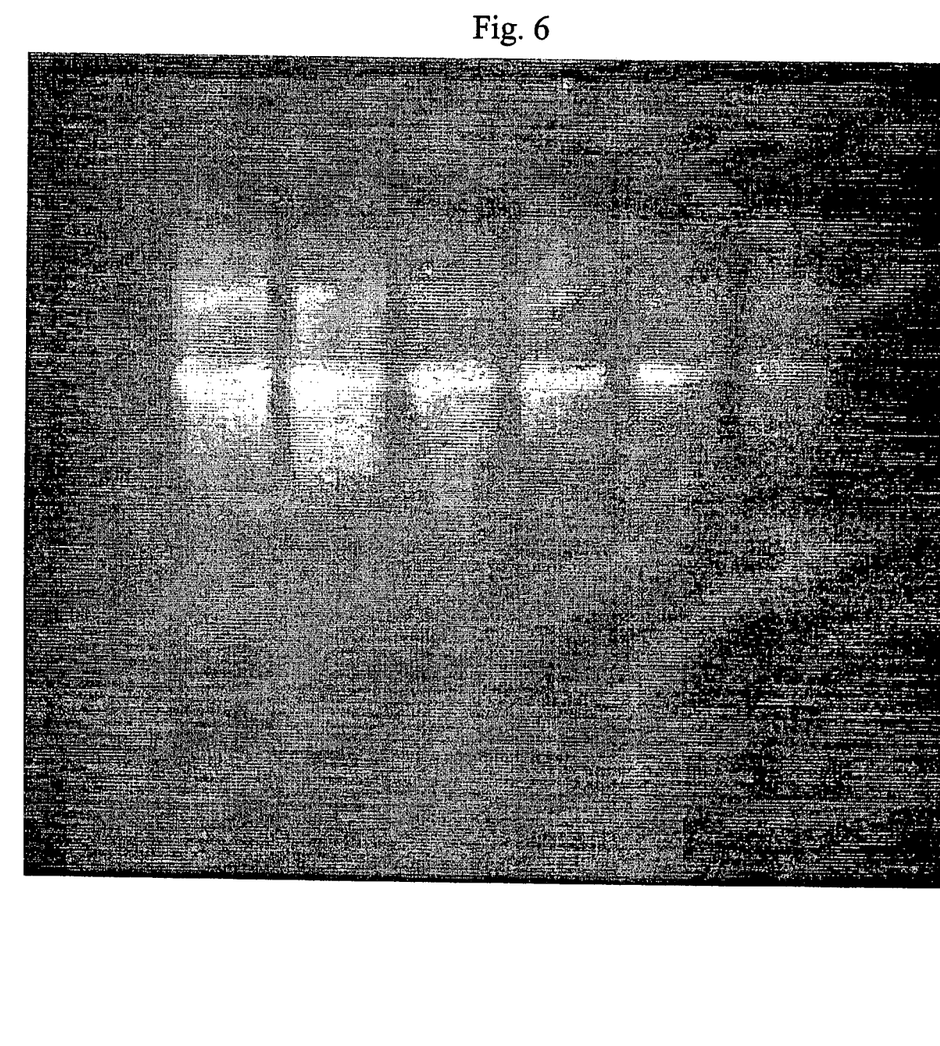
Figure 7:
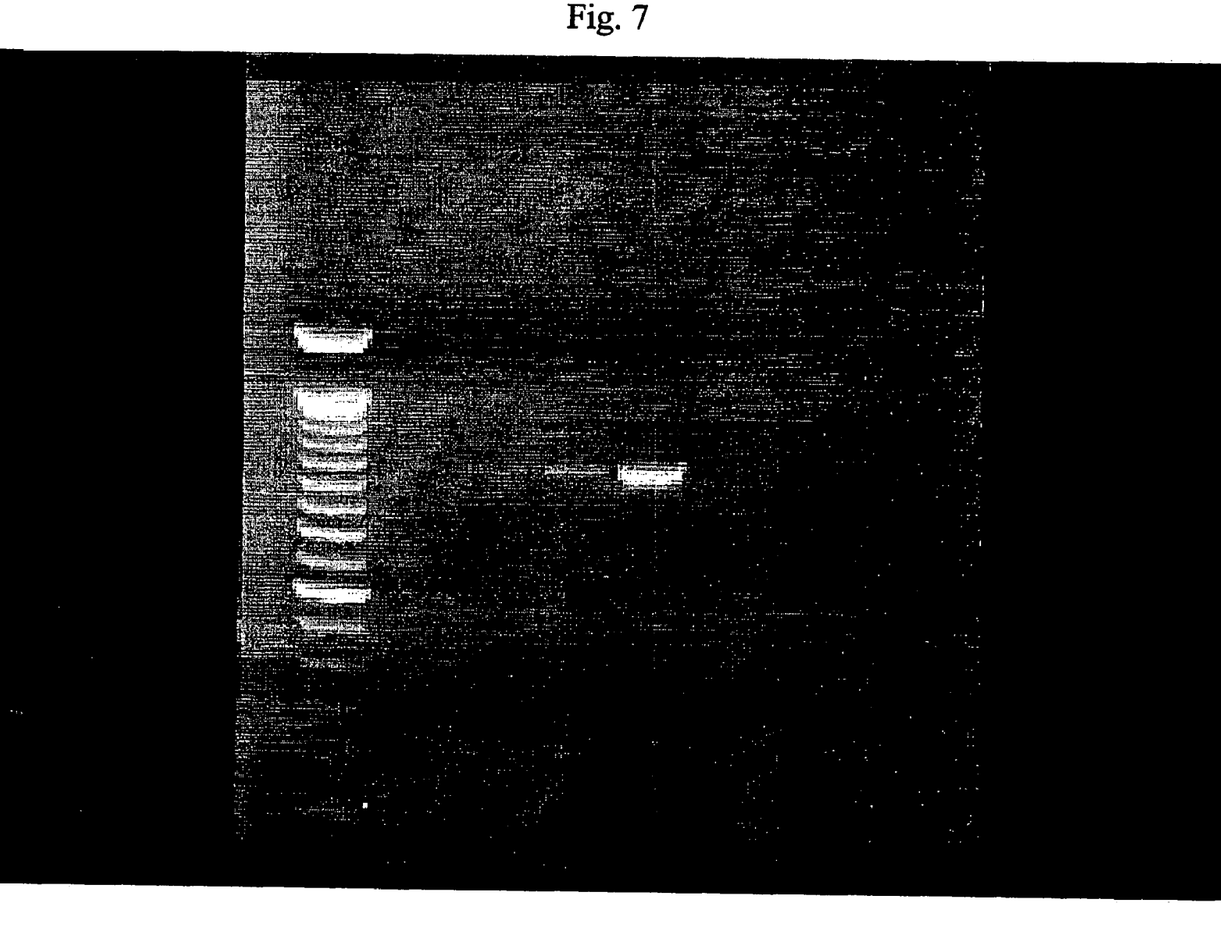
Figure 8:
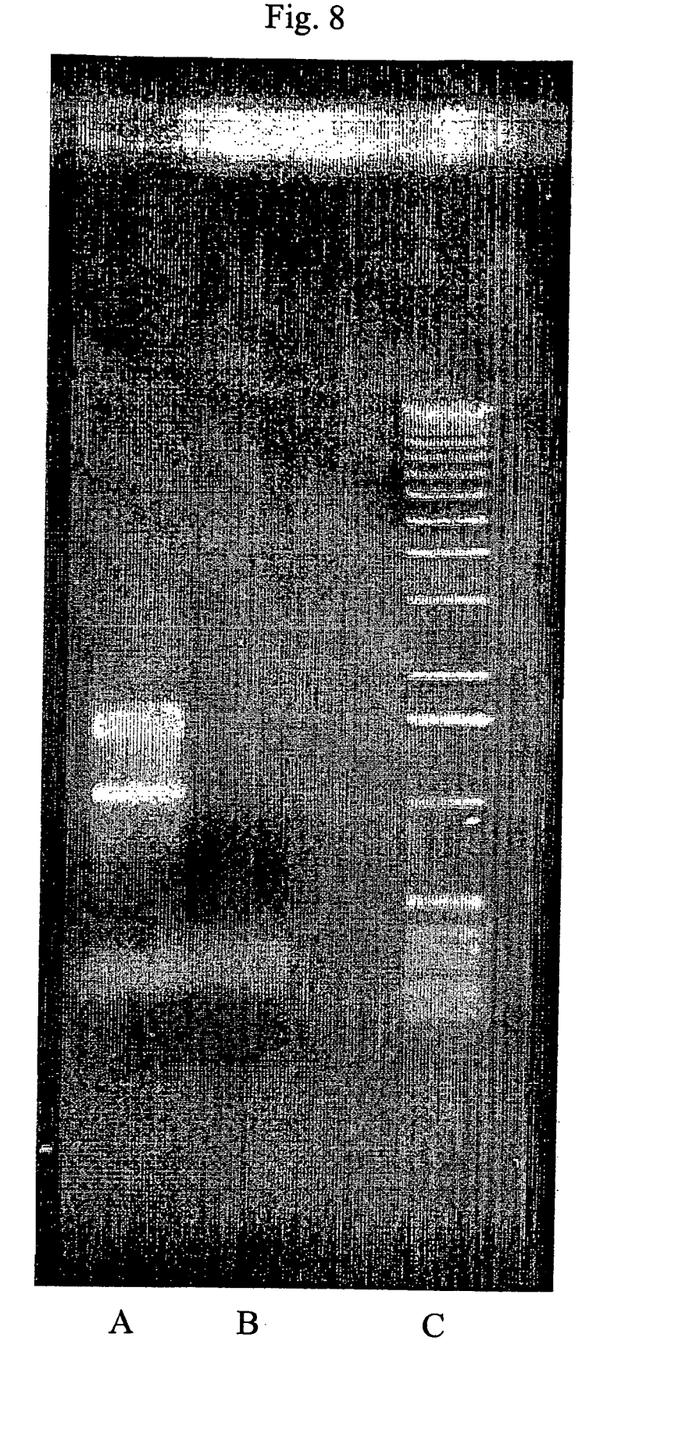

In one aspect, the present invention contemplates a method of isolating RNA from a biological specimen by first contacting the biological specimen with an admixture of (i) a mono-phasic (one phase) solution of phenol and guanidine isothiocyanate and (ii) a lysis buffer under conditions and for a time appropriate to form a homogenate. Alternatively, the RNA can be isolated from a biological specimen by contacting the biological sample first with (i) a lysis buffer, followed by (ii) a mono-phasic solution of phenol and guanidine isothiocyanate.

An admixture of (i) a mono-phasic solution of phenol and guanidine isothiocyanate and (ii) a lysis buffer is prepared according to techniques well known to workers of ordinary skill in the art. For example, prepared solutions of (i) a mono-phasic solution of phenol and guanidine isothiocyanate and (ii) a lysis buffer are manually mixed together for a time sufficient to form an admixture. Alternatively, those prepared solutions can be mixed together mechanically, such as by use of a vortex mixer (for laboratory scale mixing) or mixers, shakers, rollers and the like for industrial scale mixing. The relative proportions of mono-phasic phenol and guanidine isothiocyanate solution to lysis buffer is typically about 10:1 to about 1:1, and more usually about 5:1 to about 4:1, by volume.

The resulting admixture is then contacted with a biological specimen according to techniques well known to those of ordinary skill in the art. For example, a bacterial culture can be grown in a liquid culture medium, and a bacterial pellet prepared by ultracentrifugation. The resulting bacterial pellet can be resuspended in the admixture of the invention. Exemplary reaction times and conditions for formation of the resulting homogenate are set forth elsewhere herein. Alternatively, a fresh clinical isolate can be directly introduced into the admixture of the invention to form a homogenate.

In alternative embodiments, the method of the invention involves contacting a biological specimen first with a lysis buffer. The biological specimen can remain in contact with the lysis buffer for a time, under reaction times and conditions set forth elsewhere herein, or a mono-phasic solution of phenol and guanidine isothiocyanate can be added immediately after the lysis buffer. Once the latter solution is added, the homogenate is formed under reaction times and conditions set forth elsewhere herein.

In preferred embodiments, the methods of the invention are used for the isolation of total RNA. "Isolation of total RNA" does not necessarily mean that all RNA found in a cell is isolated, but only that a majority of the predominant RNA types have been isolated and are available for further use. For example, total RNA will typically contain substantial amounts of mRNA as well as rRNA, tRNA and other types of RNA, although not necessarily in the same percentages as those RNA types naturally exist in the biological specimen. When total RNA is isolated from eukaryotic cells, the mRNA can be further isolated from the total RNA by use of, for example, a poly(dT) column, which column selectively binds the poly(A) tail found on most eukaryotic mRNA, according to techniques well known to those of ordinary skill in the art.

The appropriate reaction conditions and times are well known to workers of ordinary skill in the art. For example, the reaction conditions can be performed at high temperatures, such as from about 90 to about 100° C., preferably about 95° C., in order to facilitate cell lysis and denaturation of protein contaminants. In such instances, the time required for cell lysis is usually brief, from about 2 to about 10 minutes, preferably about 4 minutes.

Alternatively, the reaction conditions can be performed at around normal human body temperatures, of about 37° C., but the time for cell lysis can be longer, requiring from about 10 to about 30 minutes of incubation time. Generally, as the reaction temperatures decrease, the time required for adequate cell lysis increases. Moreover, the reaction times and conditions can vary depending upon the sample size. The reaction times and conditions exemplified herein are directed to laboratory scale assays, as opposed to industrial scale assays. Nevertheless, scale up of the methods of the invention is well within the capabilities of workers of ordinary skill in the art.

Further incubation at about human body temperature, or at room temperature (from about 20 to about 24° C.) can be carried out, for times ranging from about 2 to about 10 minutes, preferably about 5 minutes.

Preferably, the biological specimen is a clinical isolate of a microorganism. These clinical isolates can be swabs, mucous samples, exudates, aspirates, biopsy samples, and the like.

The microorganism can be a bacterium, a virus, a fungus, or a combination thereof. Clinical isolates are often assayed for the presence of a microbial contaminant, such as a microorganism that is causing an infection. Rapid identification of the causative microorganism can involve the preparation of RNA samples for subsequent assays, such as RT-PCR or Northern blot analysis. Similarly, clinical isolates can be useful for forensic analysis, such as morbidity and mortality studies on infectious microorganisms.

It is to be understood, however, that the biological specimen can be of human, animal, plant or microbial origin. The invention is not limited to human infectious agents, and is adaptable to biological specimens and samples from any source that is known to contain, or may contain, an RNA of interest.

The mono-phasic solution of phenol and guanidine isothiocyanate can be prepared according to methods well known in the art, and as set forth in U.S. Pat. No. 5,346,994, whose disclosures are incorporated in their entirety herein. A mono-phasic solution of phenol and guanidine isothiocyanate is commercially available as Trizol® (Invitrogen Corp., Carlsbad, Calif.).

The lysis buffer comprises a chelating agent and a dispersing agent. However, other components can be present, such as buffering agents to provide an appropriate pH value for the resulting solution, and salts, sugars and the like to provide appropriate osmolality. The pH value of the lysis buffer can be from about 4.0 to about 6.0, preferably from about 4.8 to about 5.2, and most preferably about 5.0.

Without wishing to be bound by theory, it is believed that the chelating agent is present to chelate or sequester certain ions that can be present in the biological sample. For example, biological samples often contain magnesium or manganese ions that can be chelated with chelating agents that are well known to workers of ordinary skill in the art.

The term "chelating agent" as used herein refers to any organic or inorganic compound that will bind to a metal ion having a valence greater than one. Chelating agents include, but are not limited to, organic chelating agents such as ethylenediamene-tetraacetic acid (EDTA), triethylenetetramine dihydrochloride (TRIEN), ethylene glycol bis-(β-aminoethylether)-N,N,N',N'-tetraacetic acid (EGTA), diethylenetriamine-pentaacetic acid (DPTA), and triethylenetetramine-hexaacetic acid (TTG), deferoxamine, Dimercaprol, edetate calcium disodium, zinc citrate, penicillamine succimer and Editronate or any other chelating agent that can chelate divalent ions such as $Ca^{2+}$, $Mg^{2+}$, $Mn^{2+}$, $Fe^{2+}$, and $Zn^{2+}$.

Such chelating agents can also be selected from the group consisting of aminocarboxylates, aminophosphonates, polyfunctionally-substituted aromatic chelating agents and mixtures therein, all as hereinafter defined.

Aminocarboxylates useful as chelating agents include ethylenediaminetetracetates, N-hydroxyethylethylenediaminetriacetates, nitrilo-tri-acetates, ethylenediaminetetrapropriates, triethylenetetraaminehexacetates, diethylenetriaminepentaacetates, and ethanoldi-glycines, alkali metal, ammonium, and substituted ammonium salts therein and mixtures therein.

Aminophosphonates are also suitable for use as chelating agents in the compositions of the invention, and include ethylenediaminetetrakis-(methylenephosphonates) known commercially as DEQUEST® (available from Solutia Inc., St. Louis, Mo.). Preferably, these aminophosphonates do not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A biodegradable chelating agent is ethylenediaminedisuccinate ("EDDS"), especially the [S,S] isomer as described in U.S. Pat. No. 4,704,233, Nov. 3, 1987, to Hartman and Perkins.

The compositions herein can also contain water-soluble methyl glycine diacetic acid (MGDA) salts (or acid form) as a chelating agent. Similarly, the so-called "weak" builders such as citrate can also be used as chelating agents.

In preferred embodiments, the chelating agent is EDTA. In other preferred embodiments, the chelating agent is EGTA. In an especially preferred embodiment, the chelating agent is a combination of EDTA and EGTA. Workers of ordinary skill in the art can readily determine other chelating agents, or other combinations of chelating agents, useful in the present invention.

Without wishing to be bound by theory, the dispersing agent is believed to be present to disrupt or solubilize various components of the biological specimen. For example, a dispersing agent can disrupt a cell wall and/or cell membrane or solubilize various proteins, lipoproteins and/or lipids often found in biological samples. In some instances, preferred dispersing agents perform these functions because of surface active, or surfactant, properties of the detergents or surfactants used. However, it is not necessary for the invention that the dispersing agent has surfactant properties. A surfactant or surface-active agent can be a compound in one of three categories: a detergent, a wetting agent or an emulsifier. See, R. J. Lewis, Jr., *Hawley's, Condensed Chemical Dictionary*, 12th ed., Van Nostrand Reinhold Company, New York, 1993, page 1108. Detergents, with and without surface active properties, are well known in the art.

Natural and synthetic surfactants that are useful in the present invention include those classified as nonionic, anionic, cationic, zwitterionic or amphoteric. Non-limiting examples of such surfactants useful in the present invention, either alone or in combination, as classified by chemical type, include the following:

alcohols (such as refined soybean sterol, a nonionic surfactant);

alkanolamides (such as coconut diethanolamide, 1:1 type, a nonionic surfactant); alkanolamines (such as ethoxylated coconut monoethanolamine, a nonionic surfactant);

alkylaryl sulfonates (such as sodium alkyl aryl sulfonate, an anionic surfactant);

alkylaryl sulfonic acids (such as linear dodecyl benzene sulfonic acid, an anionic surfactant);

amine acetates (such as acetic acid salts of the n-alkyl amines, cationic surfactants);

amine oxides (such as coco amido propyl dimethyl amine oxide, cetyl dimethyl amine oxide, lauryl dimethyl amine oxide, myristyl cetyl dimethyl amine oxide, and myristyl dimethyl amine oxide, all noninonic surfactants);

amines (such as primary alkylamines and cocamidopropyl dimethylamine, both cationic surfactants); sulfonated amines and amides (such as sulfated fatty amide, amide sulfonate, and isopropylamine sulfonate, all anionic surfactants);

betaine derivatives (such as cocamidopropyl betaine, oleyl betaine, coconut alkyl dimethyl ammonium betaine, and lauramidopropyl betaine, all amphoteric surfactants);

block polymers (such as block copolymers of propylene oxide and ethylene oxide, nonionic surfactants);

carboxylated alcohol or alkylphenol ethoxylates (such as carboxylated alkyl polyether, alkyl polyethylene glycol ether acetic acid, alkylether carboxylic acid, and carboxylated alcohol ethoxylates, all anionic surfactants);

diphenyl sulfonate derivatives (such as disodium mono- and di-dodecyl diphenyl oxide disulfonate, sodium hexyl diphenyloxide disulfonate, dodecyl diphenyloxide disulfonic acid, sodium dodecyl diphenyl ether disulfonate, and disodium alkyl diphenyloxide sulfonate, all anionic surfactants);

ethoxylated alcohols (such as polyoxyethylene (4) lauryl ether, polyoxyethylene (2) cetyl ether, polyoxyethylene (10) cetyl ether, polyoxyethylene (20) stearyl ether, ethoxylated oleyl alcohol, fatty alcohol polyglycol ether, ethoxylated lauryl alcohol, ethoxylated aliphatic alcohol, and alkyl polyether, all nonionic surfactants);

ethoxylated alkylphenols (such as alkylphenol polyethylene glycol ether, nonylphenoxy polyethoxyethanol, octylphenol ethoxylate, nonylphenol ethoxylate, and octylphenoxypolyethoxyethanol, all nonionic surfactants);

ethoxylated amines and/or amides (such as fatty amine polyglycol ethers [both nonionic and cationic surfactants], polyoxyethylated (30) oleyl amine and polyoxyethylated (5) tallow amine [cationic surfactants], ethyloxylate coco amine and ethoxylated tallow amine [nonionic surfactants];

ethoxylated fatty acids (such as ethylene glycol monostearate, polyethylene glycol (400) monoricinoleate, PEG-600 monolaurate, PEG-600 dioleate, oleic acid polyglycol ester, diethylene glycol monostearate, all nonionic surfactants);

ethoxylated fatty esters and oils (such as polyoxyethylene fatty glyceride, polyoxyethylene polyol fatty acid ester, polyoxyethylene 20 sorbitan monolaurate, PEG-2 castor oil, and ethoxylated castor oil, all nonionic surfactants);

fatty esters (such as sodium stearoyl lactylate, calcium stearoyl-2-lactylate [both anionic surfactants], and butyl oleate [a nonionic surfactant]);

fluorocarbon-based surfactants (such as potassium fluorinated alkyl carboxylates, ammonium perfluoroalkyl sulfonates, and potassium perfluoroalkyl sulfonates [all anionic surfactants], fluorinated alkyl amphoteric mixture [an amphoteric surfactant], and fluorinated alkyl quaternary ammonium iodides [a cationic surfactant]);

glycerol esters (such as glycerol monolaurate, glycerol mono/dioleate, propylene glycol dicaprylate/dicaprate, decaglycerol tetracocate, triglycerol monostearate, polyglyceryl ester, and sodium stearyl lactylate, all nonionic surfactants);

glycol esters (such as PEG 400 ditallate and PEG 200 dilaurate, nonionic surfactants); heterocyclic type products (such as DL-pyrrolidone carboxylic acid salt of $N^2$cocoyl-L-arginine ethyl ester, a cationic surfactant);

imidazolines and imidazoline derivatives (such as lauric acid imidazoline and amidoimidazoline) [both cationic surfactants], and monocarboxylic coconut-based imidazoline and methyl alkyl imidazoline sodium salt [both amphoteric surfactants];

isethionates (such as sodium cocoyl isethionate, an anionic surfactant);

lanolin-based derivatives (such as lanolin-derived extracts of sterols and sterol esters [nonionic surfactants] and lanolin fatty acids [anionic or nonionic surfactants];

lecithin and lecithin derivatives (such as lecithin, hydroxylated lecithin, and soy phosphatides [amphoteric surfactants];

lignin and lignin derivatives (such as calcium lignosulfonate, an anionic surfactant); monoglycerides and derivatives (such as gylceryl moncaprylate and glyceryl monolaurate, both nonionic surfactants);

olefin sulfonates (AOS) (such as sodium alpha olefin sulfonate, an anionic surfactant); phosphate esters (such as polyoxyethylene phenyl ester phosphate, aromatic phosphate acid ester, mono- and dialkyl acid phosphate, and alkyl ether phosphate ester (free acid or potassium salt), all anionic surfactants);

phosphorous organic derivatives (such as phosphated mono- and diglycerides, phosphated nonylphenoxy ethanol, phosphated glycol ester, and phosphated linear alcohol ethoxylate, all anionic surfactants); polyethylene glycols;

polymeric [polysaccharide, acrylic acid, acrylamide] (such as $C_9$-$C_{11}$ alkyl polysaccharide, ether and alkyl polyglycosides [nonionic surfactants], and crosslinked hydrophobically-modified polyacrylic acid polymer [anionic surfactants]);

propoxylated and ethoxylated fatty acids, alcohols or alkyl phenols (such as alkoxylated alcohol, ethyoxylated and propoxylated lauryl alcohol, and linear alcohol ethoxylate, all nonionic surfactants); protein-based surfactants (such as TEA-lauroyl collagen amino acids and TEA-abietoyl-hydrolyzed animal protein [anionic surfactants], and POE (25) glycerin mono-pyroglutamic monoisostearic diester [a nonionic surfactant]);

quaternary surfactants (such as trimethyl cetyl quaternary ammonium chloride, polyoxyalkylene amine quaternary and dimethyl dicoco quaternary ammonium chloride, all cationic surfactants); sarcosine derivatives (such as sodium-N-lauryl sarcosinate, cocoyl sarcosine, and lauroyl sarcosine, all anionic surfactants);

silicone-based surfactants (such as polysiloxane polyether copolymers and silicone glycol copolymers, nonionic surfactants);

soaps (such as potassium coconut oil soap and potassium vegetable oil soap, anionic surfactants);

sodium isethionate (such as sodium salt of cocoyl isethionate in stearic acid, an anionic surfactant);

sorbitan derivatives [such as POE (20) sorbitan monolaurate, sorbitan monooleate, and POE (20) sorbitan monooleate, all nonionic surfactants];

sucrose and glucose esters and derivatives (such as sucrose distearate, ethoxylated (120) methyl glucoside dioleate, and alkylpolyglucoside, all nonionic surfactants);

sulfates and sulfonates of oils and fatty acids (such as sulfated castor oil, sulfated synthetic sperm oil, and sulfonated oleic acid, all anionic surfactants);

sulfates and sulfonates of ethoxylated alkylphenols (such as sodium or ammonium salts of sulfated polyethoxynonylphenol and sodium salt of alkylaryl polyether sulfonate, all anionic surfactants); sulfates of alcohols (such as sodium lauryl sulfate and ammonium hexyl sulfate, anionic surfactants);

sulfates of ethoxylated alcohols; sulfates of fatty esters (such as ammonium alcohol ether sulfate, ammonium laureth sulfate, and sodium alcohol ether sulfate, all anionic surfactants);

sulfates of fatty esters (such as sulfated fatty acid ester, sulfated butyl tallate, and fatty glycerin sulfate, all anionic surfactants);

sulfonates of dodecyl and tridecylbenzenes (such as sodium salt of linear alkybenzene sulfonic acid, sodium dodecylbenzene sulfonate, and sodium tridecylbenzene sulfonate, all anionic surfactants);

sulfonates of naphthalene and alkyl naphthalene (such as sodium alkyl naphthalene sulfonate, sodium n-butyl naphthalene sulfonate, and sodium diisopropyl naphthalene sulfonate, all anionic surfactants); sulfonates of petroleum (such as sodium petroleum sulfonate, an anionic surfactant);

sulfoccinamates (such as disodium N-octadecyl sulfosuccinamate, tetrasodium N-(1,2-dicarboxyethyl)-N-octadecylsulfosuccinamate, and di-ammonium N-octadecylsulfosuccinamate, all anionic surfactants);

sulfosuccinates and derivatives (such as dioctyl sulfosuccinate sodium salt, disodium lauryl sulfosuccinate, and disodium mono-oleamido PEG-2 sulfosuccinate, all anionic surfactants);

taurates (such as sodium-N-methyl-N-oleyl-taurate, an anionic surfactant);

thio and mercapto derivatives (such as polyoxyethylene thioethers and ethoxylated dodecylmercaptan, nonionic surfactants);

and tridecyl and dodecyl benzene sulfonic acids (such as modified dodecyl benzene sulfonic acid, an anionic surfactant). Further examples are given in *McCutcheon's Emulsifiers & Detergents* (McCutcheon Division, MC Publishing Co., New Jersey (1994)).

Further non-limiting examples of surfactants useful herein include the conventional. $C_{11}$-$C_{18}$ alkylbenzene sulphonates ("LAS"); the $C_{10}$-$C_{18}$ secondary (2,3) alkyl sulphates of the formula $CH_3(CH_2)_x$ $(CHOSO_3^-M^+)CH_3$ and $CH_3(CH_2)_y$ $(CHOSO_3^-M^+) CH_2CH_3$ where x and (y+1) are integers of at least about 7, preferably at least about 9, and M is a water-solubilizing cation, especially sodium; unsaturated sulphates such as oleyl sulphate; $C_{10}$-$C_{18}$ alkyl alkoxy carboxylates (especially the EO 1-7 ethoxycarboxylates); the $C_{10}$-$C_{18}$ glycerol ethers; the $C_{10}$-$C_{18}$ alkyl polyglycosides and their corresponding sulphated polyglycosides; and $C_{12}$-$C_{18}$ alpha-sulphonated fatty acid esters. If desired, the conventional nonionic and amphoteric surfactants-such as the $C_{12}$-$C_{18}$ alkyl ethoxylates ("AE") including the so-called narrow peaked alkyl ethoxylates and $C_6$-$C_{12}$ alkyl phenol alkoxylates (especially ethoxylates and mixed ethoxy/propoxy), $C_{12}$-$C_{18}$ betaines and sulphobetaines ("sultaines"), $C_{10}$-$C_{18}$ amine oxides, and the like, can also be used. The $C_{10}$-$C_{18}$ N-alkyl polyhydroxy fatty acid amides can also be used. Typical examples include the $C_{12}$-$C_{18}$ N-methylglucamides. See WO 9,206,154. Other sugar-derived surfactants include the N-alkoxy polyhydroxy fatty acid amides, such as $C_{10}$-$C_{18}$ N-(3-methoxypropyl) glucamide. $C_{10}$-$C_{20}$ conventional soaps or branched-chain $C_{10}$-$C_{16}$ soaps may also be used.

Other anionic surfactants can also be used, including salts (including, for example, sodium potassium, ammonium, and substituted ammonium salts such a mono-, di- and triethanolamine salts) of soap; $C_9$-$C_{20}$ linear alkylbenzenesulphonates; $C_8$-$C_{22}$ primary or secondary alkanesulphonates; $C_8$-$C_{24}$ olefinsulphonates; sulphonated polycarboxylic acids; alkyl glycerol sulphonates; fatty acyl glycerol sulphonates; fatty oleyl glycerol sulphates; alkyl phenol ethylene oxide ether sulphates; paraffin sulphonates; alkyl phosphates; isothionates such as the acyl isothionates; N-acyl taurates; fatty acid amides of methyl tauride; alkyl succinamates and sulphosuccinates; monoesters of sulphosuccinate (especially saturated and unsaturated $C_{12}$-$C_{18}$ monoesters); diesters of sulphosuccinate (especially saturated and unsaturated $C_6$-$C_{14}$ diesters); N-acyl sarcosinates; sulphates of alkylpolysaccharides such as the sulphates of alkylpolyglucoside; branched primary alkyl sulphates; alkyl polyethoxy carboxylates such as those of the formula $RO(CH_2CH_2O)_k$ $CH_2COO^-M^+$ wherein R is a $C_8$-$C_{22}$ alkyl, k is an integer from 0 to 10, and M is a soluble salt-forming cation; and fatty acids esterified with isethionic acid and neutralized with sodium hydroxide. Further examples are given in Surface Active Agents and Detergents (Vol. I and II by Schwartz, Perry and Berch).

Further exemplary surfactants useful in the present invention include polyoxyethylene(10)-isooctylphenyl ether (Triton®X-100); sodium dodecyl sulfate (SDS), Sarcosyl™, polysorbate 80 (Tween® 80), Tween® 85, polyoxyethylene (10) cetyl ether (Ceteth™ 10; Brij® 56), polyethylene glycol, polypropylene glycol, dansyl-polymyxin and the like. In an especially preferred embodiment, the detergent is N-lauroyl-sarcosine. In another especially preferred embodiment, the detergent is sodium lauryl sulfate.

The resulting homogenate is then admixed with a water-immiscible organic solvent under conditions and for a time appropriate to form an aqueous phase and an organic phase. The use of a water-immiscible organic solvent to form two phases is well known to workers of ordinary skill in the art, as are the reaction conditions and times. For example, an ice-cold (approximately zero ° C.) solution of a water-immiscible organic solvent can be admixed into the homogenate by rapid shaking for a relatively short period of time, from about 10 to about 60 seconds, preferably about 15 seconds.

A water-immiscible organic solvent is one which, when admixed with deionized water, forms two liquid phases separated by a phase boundary or a meniscus. Exemplary water-immiscible organic solvents are chloroform, carbon tetrachloride, isoamyl alcohol, toluene, diethyl ether, 1-bromo-3-chloropropane, and combinations thereof. In general, organic solvents with low polarity can be used as water-immiscible organic solvents. Other such water-insoluble organic solvents are well known to workers of ordinary skill in the art.

The resolution of the aqueous phase and the organic phase can be facilitated by centrifugation or ultracentrifugation, although the two phases will resolve if the sample is left undisturbed for a period of time until the two phases are visually separate. The aqueous phase is generally found above the organic phase, and the aqueous phase can be removed by techniques well known to workers of ordinary skill in the art. For example, the aqueous phase can be removed by pipetting or micropipetting, or by aspiration, or similar techniques. In the event that the aqueous phase is found below the organic phase, the aqueous phase can be recovered by simply removing the upper organic phase, discarding the upper organic phase, and retaining the aqueous phase for further analysis. These techniques are well known to workers of ordinary skill in the art.

The aqueous phase is then contacted with a $C_1$-$C_4$ lower alcohol under conditions and for a time to form a precipitated RNA. The use of a $C_1$-$C_4$ lower alcohol to precipitate RNA is well known to workers of ordinary skill in the art, as are the reaction conditions and times. For example, an ice-cold (approximately 0° C.) $C_1$-$C_4$ lower alcohol can be admixed with the aqueous phase by inversion for a relatively short period of time, from about 10 to about 60 seconds, preferably about 15 seconds, until a precipitate is formed. Preferred $C_1$-$C_4$ lower alcohols include ethanol, methanol, isopropyl alcohol, 2-propanol and 2-methyl-2-propanol. Isopropyl alcohol (isopropanol) is especially preferred. Other such $C_1$-$C_4$ lower alcohols are well known to workers of ordinary skill in the art.

The precipitated RNA is then recovered as by centrifugation and decanting of the aqueous phase, according to techniques that are well known to workers of ordinary skill in the art. For example, the precipitated RNA can be recovered by ultracentrifugation or microcentrifugation, and the resulting supernate discarded by aspiration or pouring. The precipitated RNA can comprise total RNA. The RNA or total RNA is then ready for further manipulation.

In a further embodiment, the present invention contemplates a method of isolating total RNA from a Gram-positive bacterium. Gram-positive bacteria are further exemplified elsewhere herein, and can include medically important Gram-positive bacteria that are causative agents for diseases in humans and other animals. In this embodiment, the Gram-positive bacterium is contacted with an admixture of (i) a mono-phasic solution of phenol and guanidine isothiocyanate and (ii) a lysis buffer under conditions and for a time sufficient to form a homogenate, as discussed elsewhere herein. Next, the homogenate is admixed with a water-immiscible organic solvent under conditions and for a time sufficient to form an aqueous phase and an organic phase, as discussed elsewhere herein. The aqueous phase is then contacted with a $C_1$-$C_4$ lower alcohol under conditions and for a time to form a precipitated RNA, as discussed elsewhere herein. The precipitated RNA is then recovered, as by centrifugation and decanting of the aqueous phase, as discussed elsewhere herein.

In another aspect, the invention contemplates a composition of matter comprising an admixture of (i) a mono-phasic solution of phenol and guanidine isothiocyanate and (ii) a lysis buffer. The components of this admixture are discussed more extensively elsewhere herein. The composition of matter is useful for isolating RNA or total RNA from a biological specimen, according to methods set forth herein or other such methods.

In another embodiment, the present invention comprises a kit comprising an admixture of (i) a mono-phasic solution of phenol and guanidine isothiocyanate and (ii) a lysis buffer. In a further embodiment, the present invention comprises a kit comprising (i) a mono-phasic solution of phenol and guanidine isothiocyanate and (ii) a lysis buffer.

The above kits optionally include instructions for isolating RNA from a biological specimen. Alternatively, the above kits optionally include instructions for isolating total RNA from a biological specimen. In preferred embodiments, the biological specimen is a bacterium. In especially preferred embodiments, the bacterium is a Gram-positive bacterium. The kit optionally includes vials, tubes, containers, packaging, inserts, and the like, as is well known by workers of ordinary skill in the art. For example, the admixtures and solutions of a kit of the invention are placed in appropriate vials, tubes or similar containers for each of manufacture, use, storage and shipment.

Using the kits, compositions and methods of the invention, RNA and/or total RNA can be isolated from biological specimens, including microorganisms such as bacterial species such as *Escherichia coli, Salmonella enterica, Klebsiella pneumoniae, Enterobacter cloacae, Citrobacter freundii, Morganella morganii, Hafnia alvei, Serratia mercescens, Pseudomonas aeruginosa, Helicobacter pylori, Staphylococcus aureus* and *Streptoccus pneumoniae*, fungal species (including yeast), viral species, bacteriophages, other microscopic organisms, tissue culture samples from eukaryotic or prokaryotic species, laboratory cultures of eukaryotic or prokaryotic species, clinical cultures and the like. Microorganisms include viruses (both extracellular and intracellular), bacteria (both eubacteria and archaebacteria), bacteriophages, fungi (including yeast), blood-transmitted parasites, and protozoa. Exemplary viruses include acquired immunodeficiency (HIV) virus, hepatitis A, B and C viruses, sinbis virus, cytomegalovirus, vesicular stomatitis virus, herpes simplex viruses, e.g. types I and II, human T-lymphotropic retroviruses, HTLV-III, lymphadenopathy virus LAV/IDAV, parvovirus, transfusion-transmitted (TT) virus, Epstein-Barr virus, and others known to the art. Bacteriophages include .PHI.X174, .PHI.6, .lambda., R17; T.sub.4, and T.sub.2. Exemplary bacteria include *P. aeruginosa, S. aureus, S. epidermidis, L. monocytogenes, E. coli, K. pneumonia* and *S. marcescens*. Surprisingly, RNA thus isolated is typically free from DNA contamination, as assayed by gel electrophoresis or PCR. Genomic DNA, if detected, is present in reduced amounts relative to other methods of isolating RNA or total RNA.

Medically or clinically relevant bacteria are often categorized by their ability to retain a colored dye, using the Gram stain technique well known in the art. Medically important Gram-positive bacilli that can be used in the methods of the present invention include *Actinomyces* spp., *Bifidobacterium* spp., *Clostiridim* spp., *Bacillus* spp., *Listeria* spp. *Nocardia* spp., *Corynebacterium* spp. and *Propionibacterium* spp. Medically important Gram-positive cocci that can be used in the methods of the present invention include *Staphylococcus* spp., *Streptococcus* spp., and *Peptostreptococcus* spp. Medically important Gram-negative bacilli that can be used in the methods of the present invention include *Aceinetobacter* spp., *Actinobacillus* spp., *Bordetella* spp., *Brucella* spp., *Campylobacter* spp., *Capnocytophaga* spp., *Cardiobacterium* spp., *Eikenella* spp., *Francisella* spp., *Haemophilus* spp., *Helicobacter* spp., *Kingella* spp., *Legionella* spp., *Morganella* spp., *Pasteurella* spp., *Citrobacter* spp., *Enterobacter* spp., *Escherichia* spp., *Klebsiella* spp., *Proteus* spp., *Salmonella* spp., *Shigella* spp., *Serratia* spp., *Yersinia* spp., *Pseudomonas* spp., *Flavobacterium* spp., *Xanthomonas* spp., *Burkholderia* spp., *Aeromonas* spp., *Plesiomonas* spp., and *Vibrio* spp. Medically important Gram-negative cocci that can be used in the methods of the present invention include *Neisseria* spp., *Moraxella* spp., and *Veillonella* spp.

EXAMPLES

Example 1

Preparation of RNA from Clinical Samples

An overnight (about 16 hours) culture of a clinical microbial sample was diluted in a ratio of 1 to 100 in fresh growth medium and grown to a desired optical density (OD). Approximately 1.5 milliliters of this culture were transferred to a pre-chilled microfuge tube and spun in a tabletop centrifuge at top speed for approximately 2 minutes at 4° C. The supernatant was removed, and the resulting microbial pellet was suspended in 800 microliters of Trizol® and 200 microliters of lysis buffer. The lysis buffer was preheated to 95° C. in a water bath for 15 minutes.

The lysis buffer was composed of 190 millimolar EDTA, 10 millimolar EGTA, 3.0% N-lauroylsarcosine, and 1.0 molar sodium acetate, and was prepared as follows. The ingredients were dissolved in water, with constant stirring and heating. The resulting solution was allowed to stand at 60° C. for 30 minutes and at room temperature (approximately 20°

C.) for approximately 16 hours, or overnight. Afterwards, the supernatant portion was carefully transferred to a fresh bottle without disturbing any precipitate.

The microbial pellet was mixed with the Trizol®/lysis buffer admixture by rapid pipetting. The resulting homogenate was incubated at 95° C. for 4 minutes. The homogenate was transferred to room temperature (approximately 20° C.) for 5 minutes. Next, 200 microliters of ice cold chloroform was added, and mixed by rapid shaking for 15 seconds. The resulting admixture was spun at 8000 revolutions per minute for 15 minutes at 4° C. Then, 400 microliters of the colorless, upper aqueous phase was carefully removed to a fresh microfuge tube. Next, 400 microliters of ice-cold isopropanol were added and mixed with the aqueous phase by inversion.

A precipitate was allowed to form at room temperature (approximately 20° C.) for 10 minutes. The precipitate was spun down at 8000 revolutions per minute for 10 minutes at 4° C. The supernatant was then discarded and 1 milliliter of ice cold 75 percent ethanol was added and mixed by inversion. The mixture was then spun at 5000 revolutions per minute for 5 minutes at 4° C. After removing the supernatant, the pellet was air dried for approximately 5 minutes, with care taken not to dry the pellet completely as doing so decreased the solubility of the resulting RNA. The pellet was then resuspended in 50 microliters of RNase-free water or TE buffer (10 millimolar Tris-1 millimolar EDTA). The RNA concentration was determined with a spectrophotometer, and the purity and yield of the process was determined by analyzing 1 microgram of RNA on a 1 percent non-denaturing agarose gel according to techniques well known to those of ordinary skill in the art. The RNA was then stored at −80° C. until further use.

RT-PCR was performed using 250 nanograms of RNA isolated as above with the OneStep™ RT-PCR Kit (Qiagen; Valencia, Calif., USA) according to the manufacturer's instructions. This kit contains a mixture of enzymes, in particular the Omniscript™ and Sensiscript™ reverse transcriptases and the HotStar™ Taq DNA polymerase. Forward and reverse primers were used at 0.5 micromolar concentrations and the final concentration of each dNTP was 400 micromolar. The actual RT-PCR reaction was conducted as follows: reverse transcription reaction for 30 minutes at 50° C.; initial PCR activation for 15 minutes at 95° C.; and three-step cycling (30 to 60 seconds at 94° C. for denaturation, followed by 30 seconds at 50° C. for annealing, and 1 minute at 72° C. for extension). The final extension was carried out at 72° C. for 10 minutes. Reaction products were analyzed on 1 percent agarose gels stained with ethidium bromide according to techniques well known to those of ordinary skill in the art.

Primer extension analysis was used to determine the start site of transcription and also the level of gene expression. Total RNA was isolated as set forth above. Primers were annealed to 20 micrograms of total RNA at 50° C. and primer extension was performed using 100 units of MuLV reverse transcriptase (Perkin-Elmer, Norwalk, Conn., USA) as previously described [Reisbig et al, *J. Antimicrobial Chemotherapy*, 51:1141-1151 (2003)].

Example 2

Preparation of RNA Samples Using Hot Phenol Method

On the first day of preparation, an overnight (about 16 hours) culture of a clinical isolate was diluted in a ratio of 1 to 20 in Mueller-Hinton Broth, for a total volume of 100 milliliters. The culture was incubated at 37° C. until the desired OD was obtained. Afterwards, 4 milliliters of the culture were removed and added to a test tube containing 1 milliliter of lysis buffer prewarmed to 95° C. The resulting mixture was incubated at 95° C. for 5 minutes. The hot lysate was then poured into a flask containing acidic phenol (pH value of about 4.8) pre-warmed to 68° C. and vigorously mixed for 5 minutes in a shaker water bath set to 68° C. The resulting hot phenol mixture was poured into a pre-cooled tube and chilled on ice for 5 minutes.

The tube was then centrifuged at 3100 revolutions per minute using a Sorvall H1000B rotor for 10 minutes at 2° C. The aqueous phase was removed to a new pre-chilled tube, and an equal volume of acidic phenol was added and mixed vigorously. This mixture was then centrifuged at 3100 revolutions per minute as before, and the aqueous phase removed to another pre-chilled tube. To that aqueous phase, 0.25 volumes of 10 molar LiCl was added and mixed well. A precipitate was allowed to form for 16 hours (or overnight) at 4° C.

On the second day of preparation, the sample was centrifuged at 3100 revolutions per minute for 10 minutes at 2° C., as before, and the RNA pellet was washed with 2 molar LiCl. The resulting RNA pellet was then dissolved in 400 microliters of DEPC-$H_2O$ and transferred to a microfuge tube. Then, 3 molar sodium acetate (pH 5.2) was added to a final concentration of 0.3 molar (approximately 40 microliters), and 2.5 volumes of 100 percent ethanol was added. The RNA was precipitated for at least 2 hours at −20° C., or for 30 minutes on dry ice. The RNA was pelleted by spinning in a microfuge at top speed for 10 minutes. The resulting RNA pellet was washed once with 70 percent ethanol, and the RNA pellet was resuspended in 200 microliters 1×TE buffer (pH 8.0). The RNA concentration was determined with a spectrophotometer. A one microgram sample was run on a 1 percent agarose gel to determine yield and purity of the sample according to techniques that are well known to those of ordinary skill in the art. The RNA was stored at −80° C. until further use.

Example 3

Preparation of Total RNA

An overnight (about 16 hours) culture of a bacterial specimen is diluted 1:100 and grown to a desired optical density (for example, for three hours). A 1.5 milliliter sample of the culture is transferred to a pre-chilled microfuge tube and is spun at top speed for 2 minutes at 4° C. The supernatant is removed and the resulting pellet is suspended in 200 microliters of lysis buffer (the lysis buffer is pre-heated to 95° C. for 10 to 15 minutes). This suspension is incubated at 95° C. for 4 minutes. Next, 1 milliliter of Trizol® is added.

The resulting homogenate is incubated at room temperature for 5 minutes. Then, 200 microliters of ice-cold (approximately zero degrees C.) chloroform is added, and is mixed by rapid shaking for 15 seconds. The resulting mixture is spun at 8000 revolutions per minute for 15 minutes at 4° C. Thereafter, 400 microliters of the colorless, upper aqueous phase is removed to a fresh tube (the aqueous phase is removed by pipetting from the top down).

To this aqueous phase 400 microliters of ice-cold (approximately zero degrees C.) isopropanol is added and mixed by inversion. The resulting total RNA is precipitated at room temperature (approximately 20° C.) for 10 minutes. The precipitated RNA is recovered by spinning at 8000 revolutions per minute for 10 minutes at 4° C.

The supernatant is then discarded and 1 milliliter of ice cold (approximately zero degrees C.) 75 percent ethanol is added and mixed by inversion. The sample is spun at 5000 revolutions per minute for 5 minutes at 4° C., and the supernatant again discarded. The resulting total RNA pellet is air-dried for 5 minutes, taking care not to completely dry the pellet, as doing so will decrease the solubility of the resulting total RNA. The air-dried total RNA is then resuspended in 50 microliters of RNase-free water or TE buffer.

The foregoing description and the examples are intended as illustrative and are not to be taken as limiting. Still other variations within the spirit and scope of this invention are possible and will readily present themselves to those skilled in the art.

Each of the patents and articles cited herein is incorporated by reference. The use of the article "a" or "an" is intended to include one or more.

We claim:

1. A method of isolating RNA from a biological specimen comprising:
    (a) contacting the biological specimen with an admixture of (i) from about 750 to about 1000 microliters of a mono-phasic solution of phenol and guanidine isothiocyanate, and (ii) from about 100 to about 300 microliters of a lysis buffer under conditions and for a time appropriate to form a homogenate;
    (b) admixing the homogenate with a water-immiscible organic solvent under conditions and for a time appropriate to form an aqueous phase and an organic phase;
    (c) contacting the aqueous phase with a $C_1$-$C_4$ lower alcohol under conditions and for a time to form a precipitated RNA; and
    (d) recovering the precipitated RNA wherein the lysis buffer compromises a chelating agent and a dispersing agent, and the biological specimen is a bacterium.

2. The method of claim 1 wherein said biological specimen is first contacted with a lysis buffer followed by a mono-phasic solution of phenol and guanidine isothiocyanate.

3. The method of claim 1 wherein the RNA isolated is total RNA.

4. The method of claim 3 wherein said biological specimen is a Gram-positive bacterium.

5. The method of claim 1 wherein the biological specimen is a clinical isolate of a microorganism.

6. The method of claim 5 wherein the biological specimen is obtained from a human, animal, plant or microbe.

7. The method of claim 1 wherein the chelating agent is EDTA, EGTA, or a combination of both.

8. The method of claim 1 wherein the dispersing agent is a detergent.

9. The method of claim 1 wherein the dispersing agent is a surfactant.

10. The method of claim 9 wherein the surfactant is N-lauroylsarcosine, sodium lauryl sulfate or a mixture thereof.

11. The method of claim 1 wherein the water-immiscible organic solvent is chloroform, carbon tetrachloride, or a mixture thereof.

12. The method of claim 1 wherein the $C_1$-$C_4$ lower alcohol is ethanol, methanol or isopropyl alcohol.

13. The method of claim 1 wherein said admixture comprises from about 750 to about 850 microliters of said mono-phasic solution of phenol and guanidine isothiocyanate and from about 150 to about 250 microliters of said lysis buffer.

14. The method of claim 1 wherein said admixture comprises about 800 microliters of said mono-phasic solution of phenol and guanidine isothiocyanate and about 200 microliters of said lysis buffer.

* * * * *